United States Patent
Coelho et al.

(10) Patent No.: US 6,302,327 B1
(45) Date of Patent: Oct. 16, 2001

(54) METHOD AND APPARATUS FOR CRYOGENIC STORAGE OF THERMOLABILE PRODUCTS

(75) Inventors: Philip H. Coelho, El Dorado Hills, CA (US); Pablo Rubinstein, New York, NY (US); Mark Buckley; Kevin Pelletier, both of Rancho Cordova, CA (US)

(73) Assignee: ThermoGenesis, Corp., Rancho Cordova, CA (US)

( * ) Notice: Subject to any disclaimer, the term of this patent is extended or adjusted under 35 U.S.C. 154(b) by 0 days.

(21) Appl. No.: 08/876,279

(22) Filed: Jun. 16, 1997

(51) Int. Cl.[7] .................................................. G06K 15/00
(52) U.S. Cl. ........................................... 235/383; 235/375
(58) Field of Search ................... 235/381, 383, 235/375, 462.13; 62/60, 514 R, 69, 78, 64, 51.1, 337

(56) References Cited

U.S. PATENT DOCUMENTS

| | | |
|---|---|---|
| 3,662,565 | 5/1972 | Gram . |
| 4,018,911 | 4/1977 | Lionetti et al. . |
| 4,090,374 | 5/1978 | Faust et al. . |
| 4,245,483 | 1/1981 | Murai . |
| 4,432,214 | 2/1984 | Richelli et al. . |
| 4,551,992 * | 11/1985 | Sitte et al. ........................ 62/514 R |
| 4,712,607 | 12/1987 | Lindemans et al. . |
| 4,757,692 * | 7/1988 | McDonald .............................. 62/69 |
| 4,814,592 * | 3/1989 | Bradt et al. ........................... 235/381 |
| 4,903,493 * | 2/1990 | Van Iperen et al. ..................... 62/60 |
| 4,920,763 | 5/1990 | Provest et al. . |
| 5,125,240 | 6/1992 | Knippscheer et al. . |
| 5,176,202 | 1/1993 | Richard . |
| 5,233,844 | 8/1993 | Knippscheer et al. . |
| 5,309,723 | 5/1994 | Thomas et al. . |
| 5,638,686 * | 6/1997 | Coehlo et al. ........................ 62/51.1 |
| 5,880,443 * | 3/1999 | McDonald ................... 235/375 |
| 5,964,095 * | 10/1999 | Coehlo et al. ........................... 62/62 |

FOREIGN PATENT DOCUMENTS

| | | |
|---|---|---|
| 411224 | 2/1991 | (EP) . |
| 4507283 | 12/1992 | (JP) . |
| 6509782 | 11/1994 | (JP) . |
| WO 9102202 | 2/1991 | (WO) . |
| WO 9102203 | 2/1991 | (WO) . |
| WO 9109521 | 7/1991 | (WO) . |
| WO 9216800 | 10/1992 | (WO) . |
| WO 9303891 | 3/1993 | (WO) . |
| WO 96/26402 | 8/1996 | (WO) . |

* cited by examiner

Primary Examiner—Karl D. Frech
(74) Attorney, Agent, or Firm—Bernhard Kreten

(57) ABSTRACT

A system and method for controlled rate freezing and storage of thermolabile substances. The system includes a storage unit for receiving product stored within a bag and an overlying protective canister associated with a robotic arm and reading device which places the canister in the preserving environment. A control system, driven by a computer monitors the ingress, egress and storage location and particularized profiles of the articles being placed in storage.

21 Claims, 16 Drawing Sheets

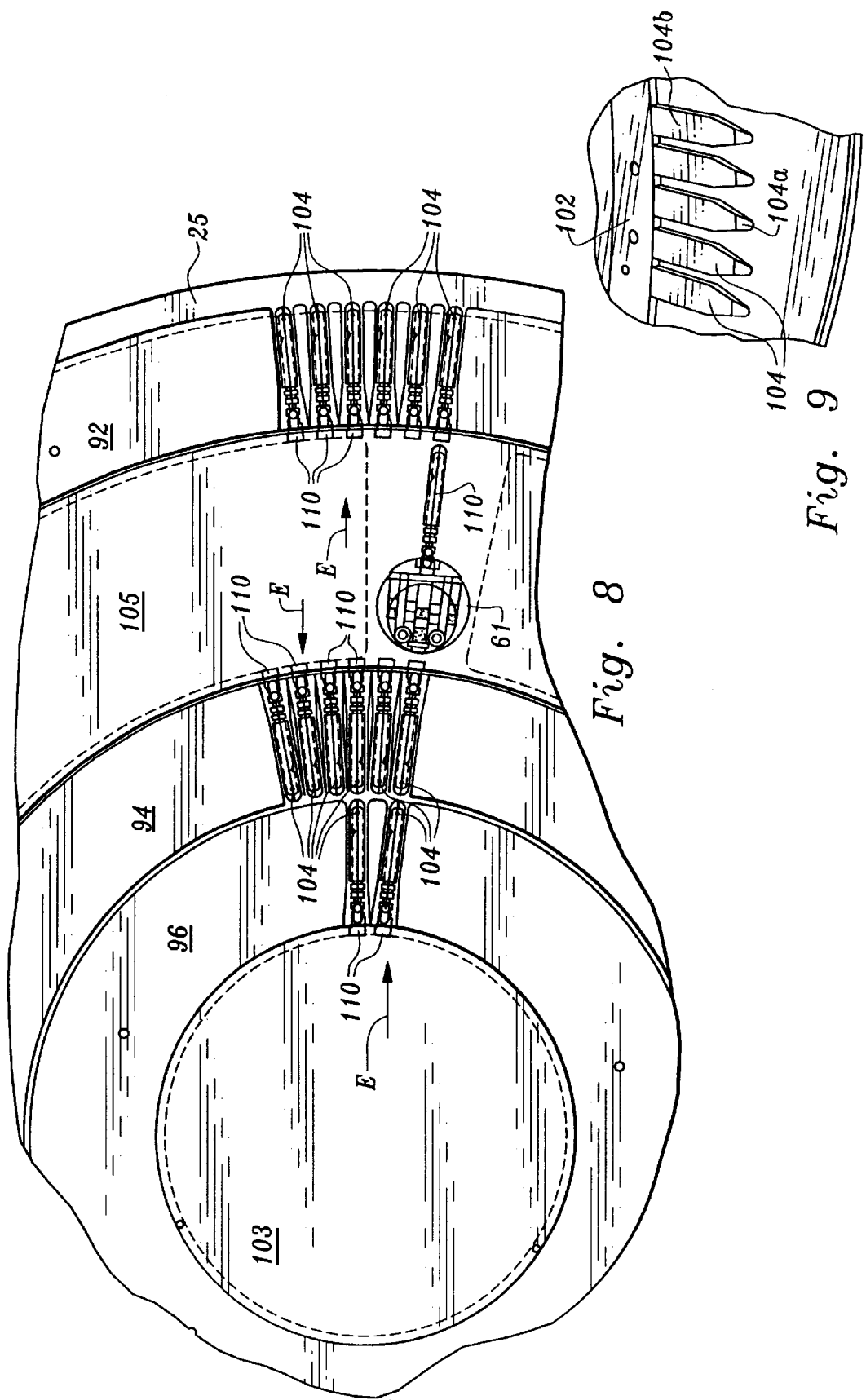

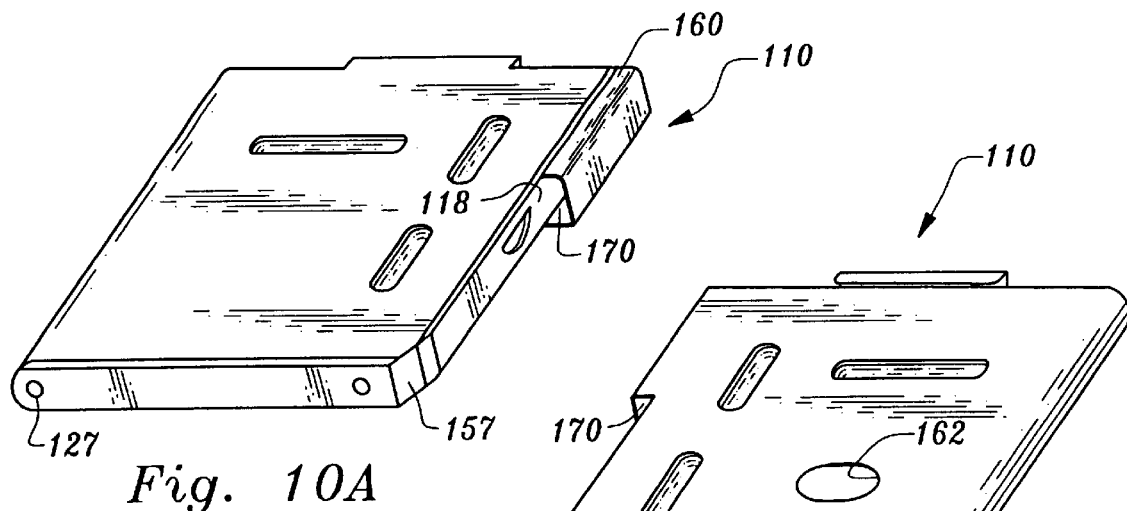
Fig. 10A
Fig. 10B
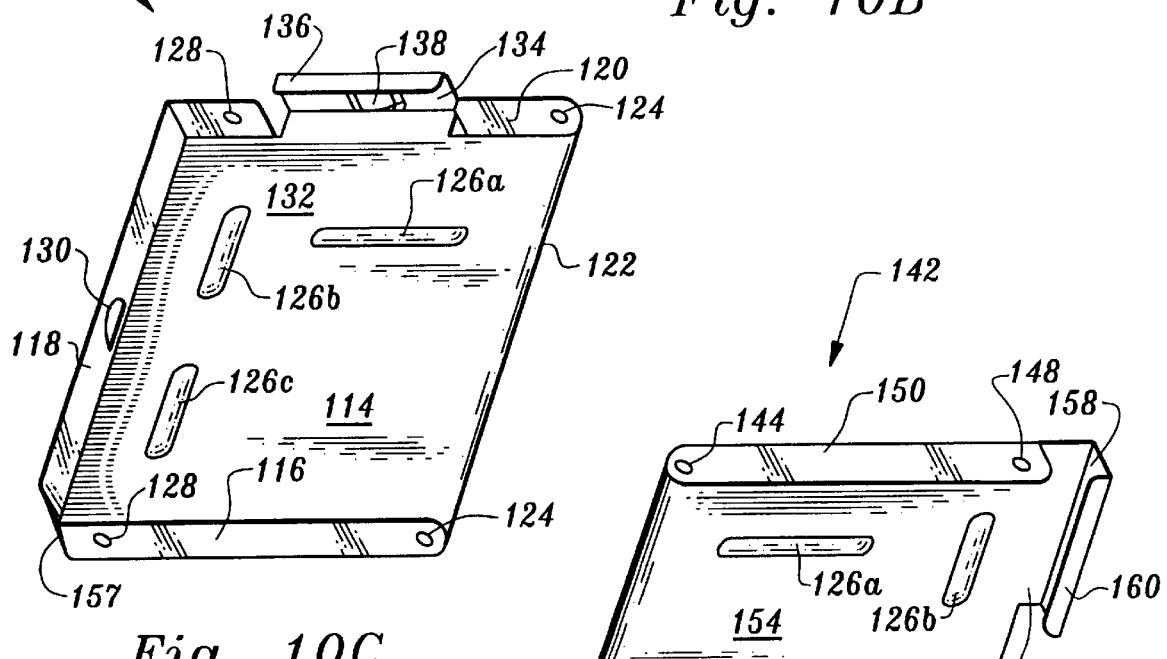
Fig. 10C
Fig. 10D

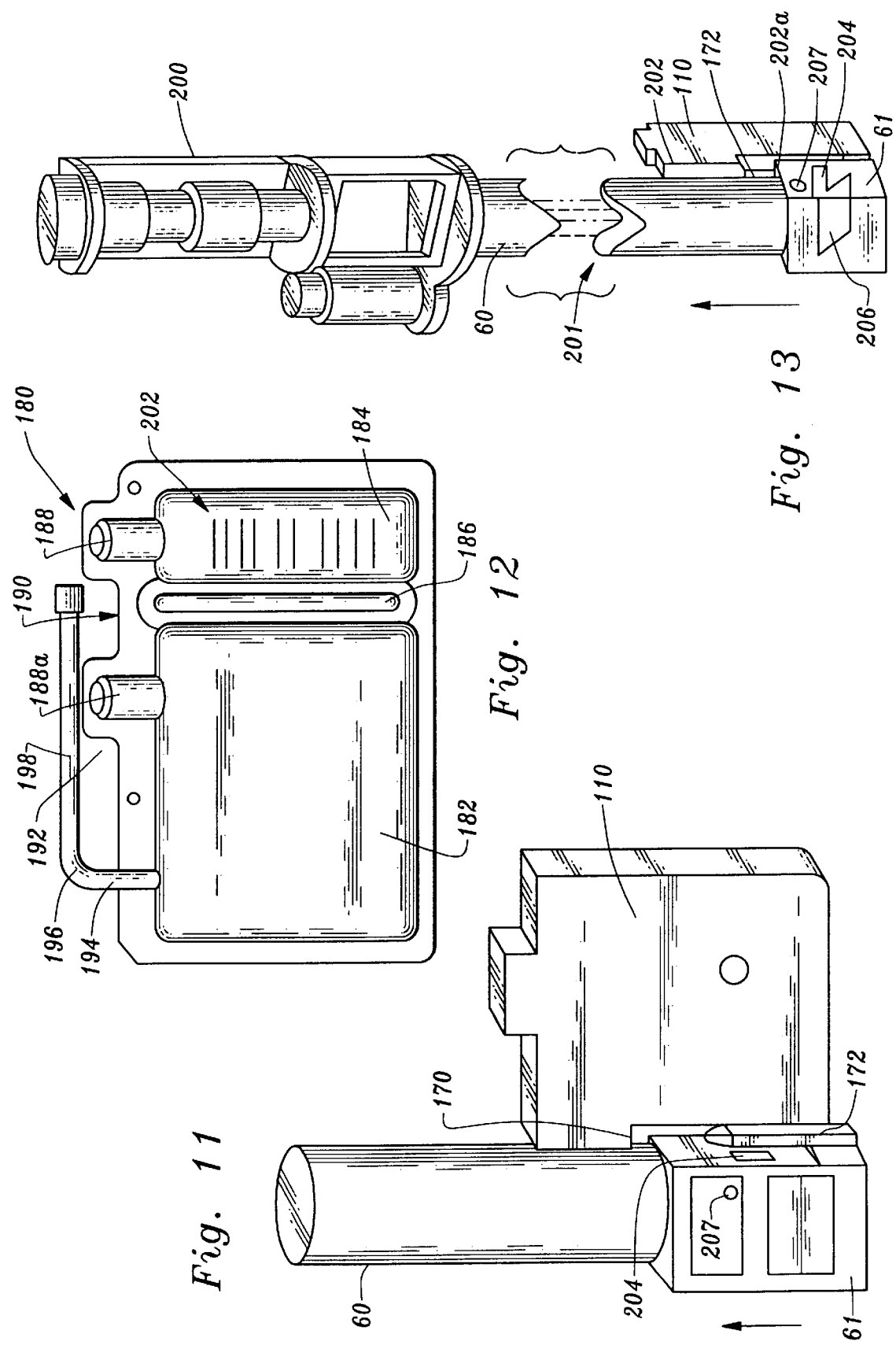

METHOD AND APPARATUS FOR CRYOGENIC STORAGE OF THERMOLABILE PRODUCTS

FIELD OF THE INVENTION

The following invention relates generally to a method and apparatus for storing a plurality of thermolabile products in a cold, preserving medium including storage addresses for each product in a cold storage dewar. Each product stored has a unique identity which correlates with both its source of origin and its location in the dewar. The device includes means for reading at least one of those identities. More specifically, this device especially enables tissue, DNA specimens, laboratory assays, certain blood products and especially white blood cells to be cryoprotected, decreased in temperature at a preprogrammed, controlled rate stored and subsequently accessed upon appropriate identification to be surrendered for subsequent use.

BACKGROUND OF THE INVENTION

This application chronicles the ongoing evolution of assignee's cryogenic storage device described in Ser. No. 08/393,558 filed Feb. 23, 1995. The need to save thermolabile products, especially in the field of medicine and for its evidentiary value in law, continues to increase. Tissue sample, DNA specimens and laboratory assays are all examples of substances which, once studied, typed and matched are suitable candidates for subsequent storage should the need ever arise for further analysis. Products which can degrade as a function of time and temperature have little archival value unless properly preserved and maintained.

Significant advances in the state of the art in blood cell research, especially sequestering and preserving white blood cells and the discovery that these cells can be used between unrelated donors and recipients, has created a need for a reliable freezing and storage device for the blood products, especially blood cells to maintain their quality prior to utilization. Although there is no longer an absolute requirement that donors and recipients be related, matching characteristics of the donor and the recipient presently optimizes the likelihood of acceptance by the recipient rather than rejection. Based on a multiplicity of factors, it is estimated that optimally matching a donor to a recipient may require selecting from an aggregation of donor specimens numbering in the thousands or even hundreds of thousands.

The problem associated with storing large numbers of donor's products is that they are thermolabile and therefore can degrade as a function of time when they are not frozen at a controlled rate and then maintained in an extremely low-temperature, controlled environment. Equally as important, once the products are stored in the appropriate low temperature environment, it is still highly desirable that the product remain stable and undisturbed at that temperature until the product is to be used. This assures the highest quality.

These foregoing considerations provide considerable engineering problems, especially should the products be stored at temperatures where nitrogen is the cold storage liquid, because mechanisms working in such an operating environment would have to be durable at −190° C. At such low temperatures, tasks which are relatively simple at room temperature, e.g. storing, selecting and removing products provide difficulties. Mechanical implements can be prone to failure at extremely low temperatures. Should there be a mechanical failure without adequate accommodation for some type of system redundancy, there can be dire consequences both as to timely treatment and as to maintaining product quality because of failure to access or maintain the product at a constant temperature.

The following patents reflect the state of the art of which applicant is aware insofar as these patents appear germane to the process at hand. However, it is stipulated that none of these patents singly nor when considered in any conceivable combination teach the nexus of the instant invention as set forth hereinabove and as particularly claimed.

| PATENT NO. | ISSUE DATE | INVENTOR |
|---|---|---|
| U.S. PATENT DOCUMENTS | | |
| 3,662,565 | May 16, 1972 | Gram |
| 4,090,374 | May 23, 1978 | Faust, et al. |
| 4,245,483 | January 20, 1981 | Murai |
| 4,432,214 | February 21, 1984 | Richelli, et al. |
| 4,920,763 | May 1, 1990 | Provest, et al. |
| 5,125,240 | June 30, 1992 | Knippscheer, et al. |
| 5,176,202 | January 5, 1993 | Richard |
| 5,233,844 | August 10, 1993 | Richard |
| FOREIGN PATENT DOCUMENTS | | |
| EP0 411 224 A2 | February 2, 1991 | Knippscheer, et al. |
| WO91/02202 | February 21, 1991 | Richard |
| WO91/02203 | February 21, 1991 | Knippscheer, et al. |
| WO91/09521 | July 11, 1991 | Richard |
| WO92/16800 | October 1, 1992 | Knippscheer, et al. |
| WO93/03891 | March 4, 1993 | Knippscheer, et al. |
| JP4-507,283 | December 17, 1992 | Knippscheer, et al. |
| JP6-509,782 | November 2, 1994 | Knippscheer, et al. |

The several patents to Knippscheer, et al. teach the use of a storage device for cryoprotecting thermolabile products including means for selectively extracting certain products upon demand. All these prior art teachings can be collectively characterized as requiring complex mechanical mechanisms whose moving components are required to perform reliably at a temperature in which liquid nitrogen is intended to be present. Because relative motion of mechanical implements is described, maintenance, repair and lubrication of the implements and reliability at such low temperatures is a grave concern. The instant invention is distinguished over the Knippscheer, et al. patents, inter alia, in that no moving components have drive mechanisms that contact or operate directly in the liquid nitrogen.

SUMMARY OF THE INVENTION

The instant invention solves the problems which plague the prior art in a multiplicity of ways. The instant invention provides a sealed dewar having a series of annular racks, preferably cylindrical in configuration and concentrically disposed therewithin. Each of the racks is maintained in a fixed position with respect to peripheral walls of the dewar. Liquid nitrogen covers the racks. Each annular rack is separated one from the other by an annular passageway. The annular passageways provide access to the racks and therefore to thermolabile products which are stored in the racks.

Head space is provided between a surface of the liquid nitrogen and an uppermost extremity of the dewar. The head space is provided with nitrogen gas to form a gas cap to continue maintaining a low temperature. An access portal is also located above the liquid level to communicate with the ambient conditions.

The upper extremity of the dewar is closed. The enclosure may include the following structure. First, the overlying enclosure is sealed. Specifically, a lid overlies the topmost extremity of the dewar. This lid prevents the nitrogen gas from escaping and provides a thermal barrier. Insulation is also provided in the lid. Thus, the lid provides a barrier to prevent both heat and ambient moisture contained in air from migrating into the dewar.

Second, the enclosure provides a support structure for a robotic arm drive mechanism. A robotic arm connects to the drive mechanism and extends through the lid to access the racks and the thermolabile products contained in the racks via the annular passageways. The robotic arm can move to selected sites in the racks and transfer thermolabile products from the racks to the access portal located on the lid and back. The robotic arm also includes an indexing mechanism which initializes and orients the arm with respect to its position vis-a-vis a reference, which perhaps is fixed in the dewar. The robotic arm includes means for reading indicia either contained on an exposed surface of the thermolabile product, or on a holder which encapsulates the thermolabile product. The robotic arm transmits that information from the thermolabile product or holder to a remote reading and memory site. The desirability of orienting and indexing of the robotic arm, coupled with its remote reading and memory capability increases the likelihood that only the desired thermolabile product is extracted from the dewar. In the case of insertion of the thermolabile product into the dewar, the storage address of the thermolabile product will be known.

OBJECTS OF THE INVENTION

Accordingly, it is a primary object of the present invention to provide a new, novel and useful method and apparatus for cryogenic storage of thermolabile products.

A further object of the present invention is to provide a device as characterized above which is extremely durable in construction, safe to use, and lends itself to mass production.

A further object of the present invention is to provide a device as characterized above in which the extreme low temperature operating environment is below all moving machinery associated therewith for added reliability and freedom from maintenance problems.

A further object of the present invention is to provide a device as characterized above in which thermolabile products that are stored at cryogenic temperatures can be delegated to a specific address in the storage device and remain there until subsequently needed.

A further object of the present invention is to provide a device as characterized above in which each thermolabile product contained in storage is first scanned for verification purposes to increase the likelihood that only the correct product is being removed from storage so as to prevent unwanted temperature excursions, particularly temperature elevations, of the product.

A further object of the present invention is to provide a device as characterized above in which each thermolabile product contained in storage is first scanned prior to removal to increase the likelihood that only the correct product is being removed from storage so as to minimize any physical disturbance of the product until such removal is desired.

Viewed from a first vantage point, it is an object of the present invention to provide an apparatus for cryopreserving a thermolabile product, comprising, in combination: a dewar, a lid sealing the dewar, a cryogenic liquid in the dewar, ullage between a top of the liquid and the lid, a portal passing through the apparatus to insert the product therethrough, robotic arm means on said apparatus for passing the product in and out of the portal, and a freezer module overlying the portal.

Viewed from a second vantage point, it is an object of the present invention to provide a method for storing thermolabile products, the steps including: scanning an identity of a product to be stored, loading the product into a deployment module, inserting the module into a freezer/storage device, controlling a temperature profile of the product to conform to an exemplar by modifying a heat transfer rate of the product, storing the product by removal of the product from the module and noting the location of the product.

Viewed from a third vantage point, it is an object of the present invention to provide a canister for receiving a thermolabile product, comprising, in combination: a receiver to accept the product, a door on the receiver to occlude and protect the product when the door is deployed, attachment means to be releasably engaged by a robotic arm, and indicia on the canister readable by means on the robotic arm to correlate with the product.

These and other objects will be made manifest when considering the following detailed specification when taken in conjunction with the appended drawing figures.

BRIEF DESCRIPTION OF THE DRAWINGS

FIG. 8 is a fragmented top view depiction of the storage rack and a robotic arm for deployment and retrieval of canisters within the dewar.

FIG. 9 is perspective view of retention projections used to retain canisters within the dewar.

FIGS. 10A through 10D are perspective views of the canister and canister elements.

FIG. 11 is a schematic depiction of a robotic arm addressing the canister.

FIG. 12 is a front view of a bag deployed within the canister of FIG. 10.

FIG. 13 is view of FIG. 11 showing an upper end of the periscope robotic arm receiving information from the canister.

DESCRIPTION OF PREFERRED EMBODIMENT

Figure 1:
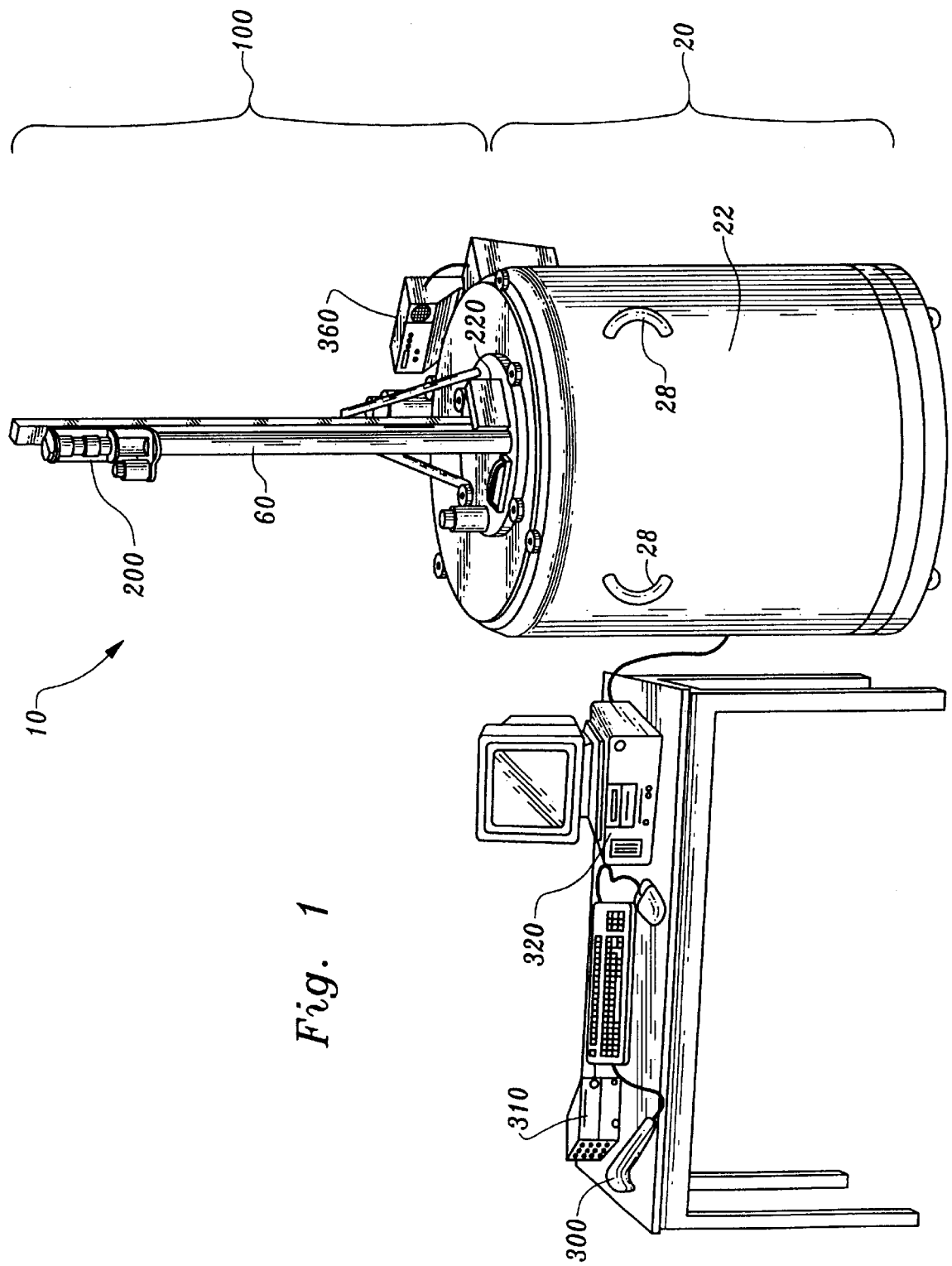
FIG. 1 is a diagrammatic depiction of the system according to the present invention.

Referring to the drawing, wherein like numerals denote like parts throughout the various figures, reference numeral 10 is directed to the apparatus according to the present invention.

Figure 2:
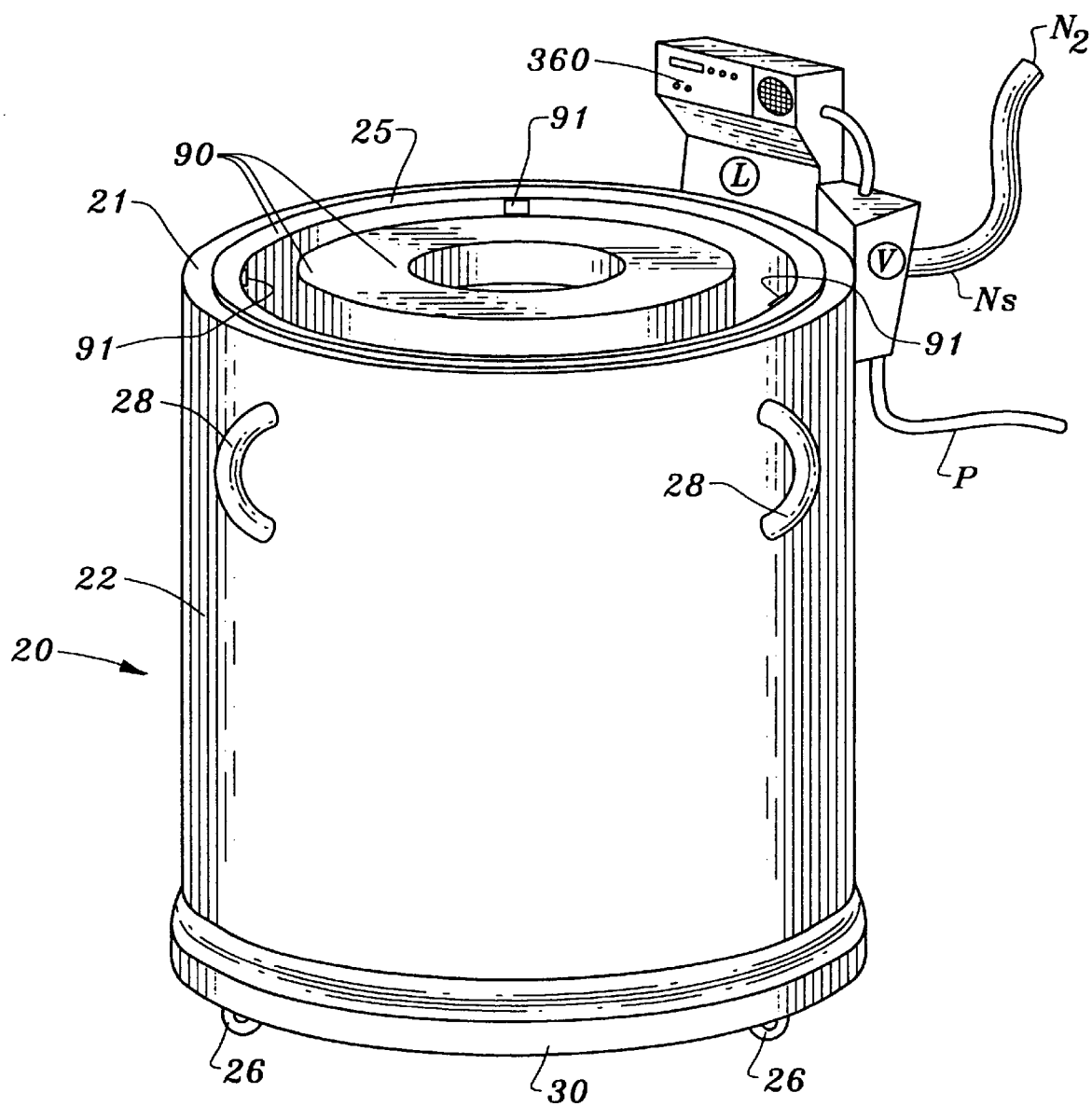
FIG. 2 is a perspective view of one component, the liquid nitrogen storage unit, isolated from its environment showing further detail.

In essence, and as shown in FIG. 1, the apparatus 10 includes a liquid nitrogen storage unit 20 within which storage racks 90 (FIG. 2) are deployed. A topmost portion of the storage unit includes a controlled rate freezing unit 100 that consists of a freezer module 220, a control module 360 and a robotic arm and periscope 60. The control module 360 monitors the environment associated with the liquid nitrogen storage unit. The freezer module 220 controls the rate at which product is decreased in temperature prior to storage in the liquid nitrogen storage unit 20 and also receives product from the liquid nitrogen storage unit 20 for retrieval. This freezer module 220 is driven by a computer 320 as is the robotic arm and periscope 60 for locating product within the liquid nitrogen storage unit 20 and retrieval. The computer 320 downloads to the freezer module 220 the profile of a temperature curve (e.g., FIG. 17), and freezer module 220 controls the downward temperature excursion of the product prior to its journey towards storage. The computer 320 also maintains a complete record as will be described. In addition, a bar code scanner 300 is associated with the computer 320 to read the identity of the product contained within a bag 180 (FIG. 12) which holds the product. A printer 310 is included which generates a label 202 (FIG. 13) for use on a canister 110 which ensconces the product and bag 180 prior to its deployment within the liquid nitrogen storage unit 20. More particularly, and with reference to FIGS. 2 and 3, the liquid nitrogen storage unit 20 consists of a dewar 22 having first and second spaced parallel walls (an outer wall 22a and an inner wall 22b) held in spaced concentric relationship and provided with a vacuum therebetween. Insulation may also be disposed between the inner and outer walls 22b, 22a. A bottom wall 22c completes the dewar 22 to define an open topped blind bore. The bottom wall 22c is supported on a platform 24 which includes a plurality of casters 26 on a bottom surface thereof so that the device 20 can be easily moved from one site to another. Handles 28 (FIG. 2) facilitate the ability of the liquid nitrogen storage unit 20 to be moved from site to site in conjunction with the casters 26 and platform 24.

Figure 4:
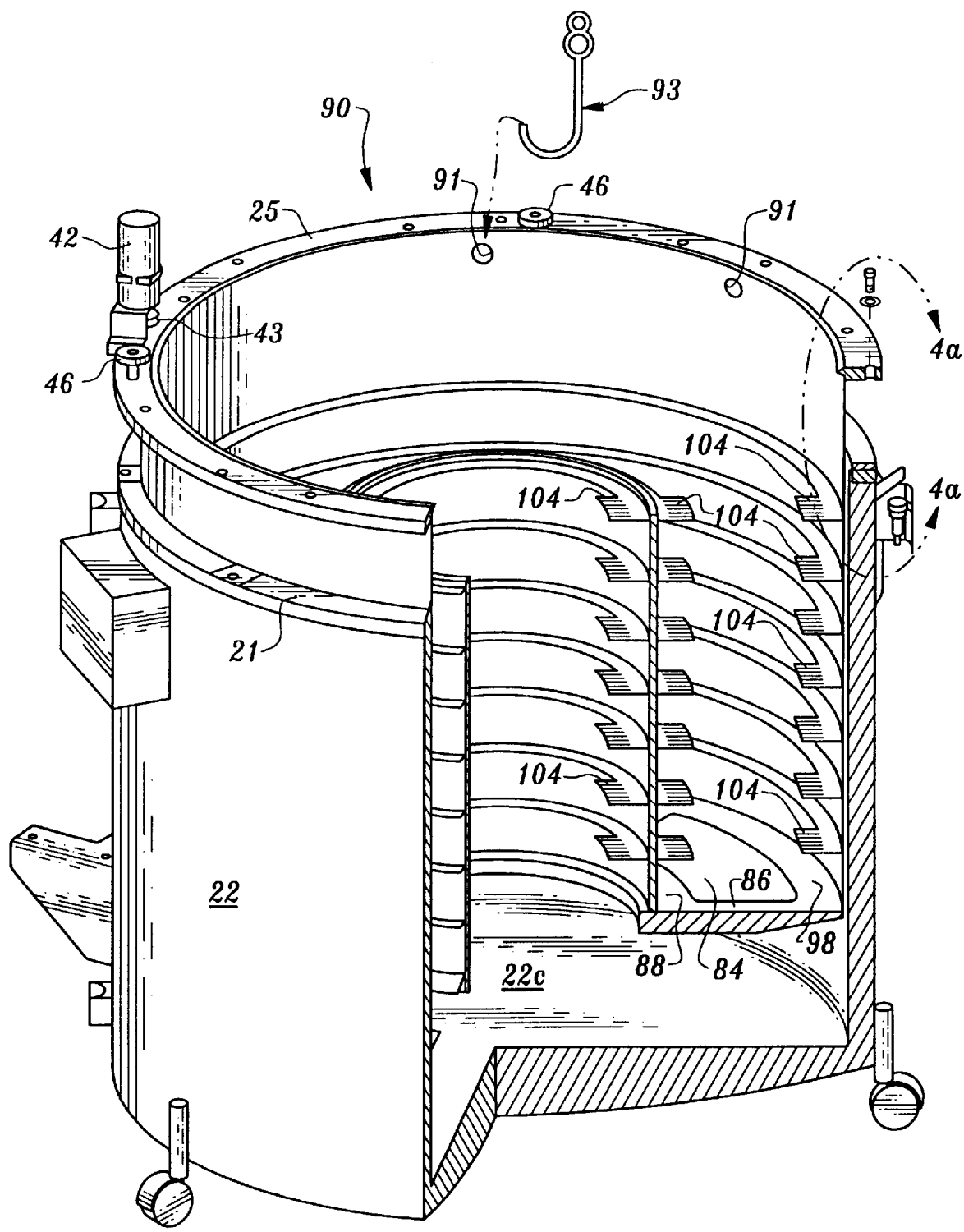
FIG. 4 is a perspective view partially fragmented showing a detail of the rack and dewar FIG. 4A reflects a detail of FIG. 4.

FIG. 4 shows a fragmentary portion of the dewar 22 enlarged (compared to FIG. 2) to reveal a radially extending lip 25 of the rack 90 overlying a top edge 21 of the dewar 22. The lip 25 suspends the rack 90 in the dewar. Recesses 91 are located strategically around the rack 90 adjacent the lip 25 each to receive a hook 93 so that the rack 90 can be removed from the dewar in its entirety including plural canisters 110 retained on projections 104 as will be described.

Figure 4A:
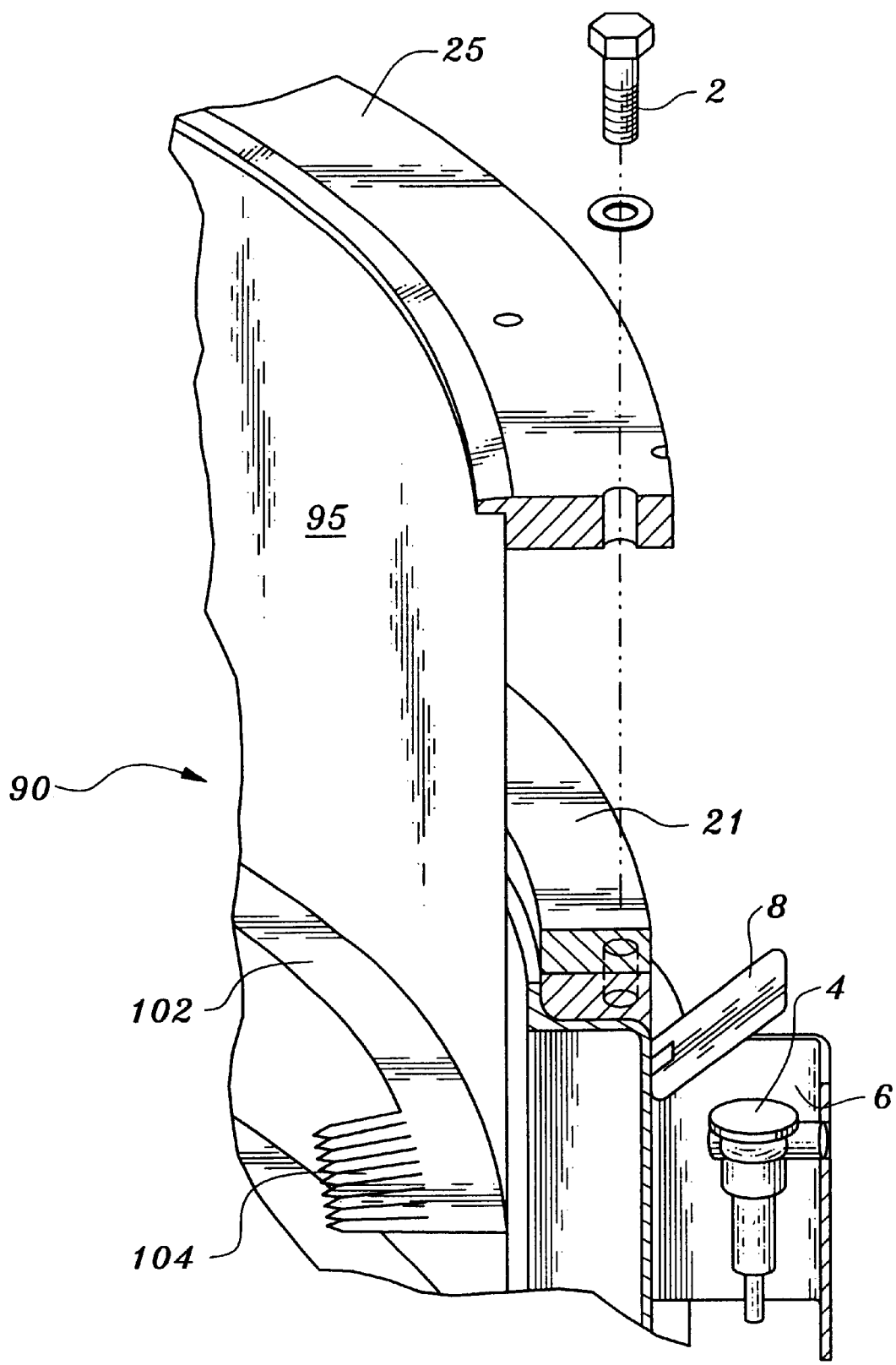

FIG. 4A shows bolts 2 used to fix the rack lip 25 to the dewar top edge 21. A kill switch 4, protected by a casing 6 and a flap 8 disables motors 42, 52 and 80 as well as linear actuator threaded rod 66 should an operator want to override the computer driving robotic device 60.

Figure 3:
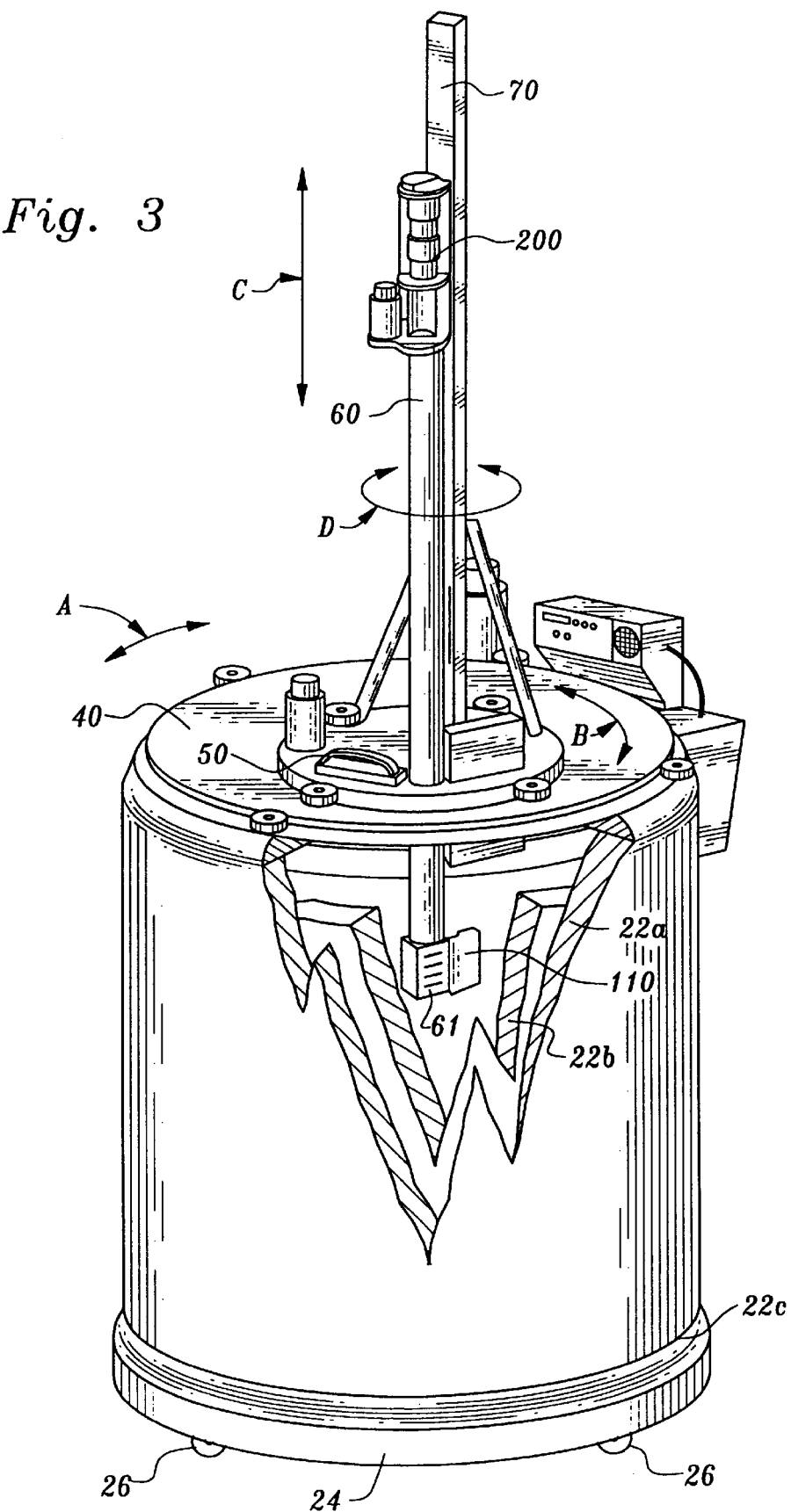
FIG. 3 greater detail of the liquid nitrogen storage unit in combination with a controlled rate freezing unit.
Figure 5:
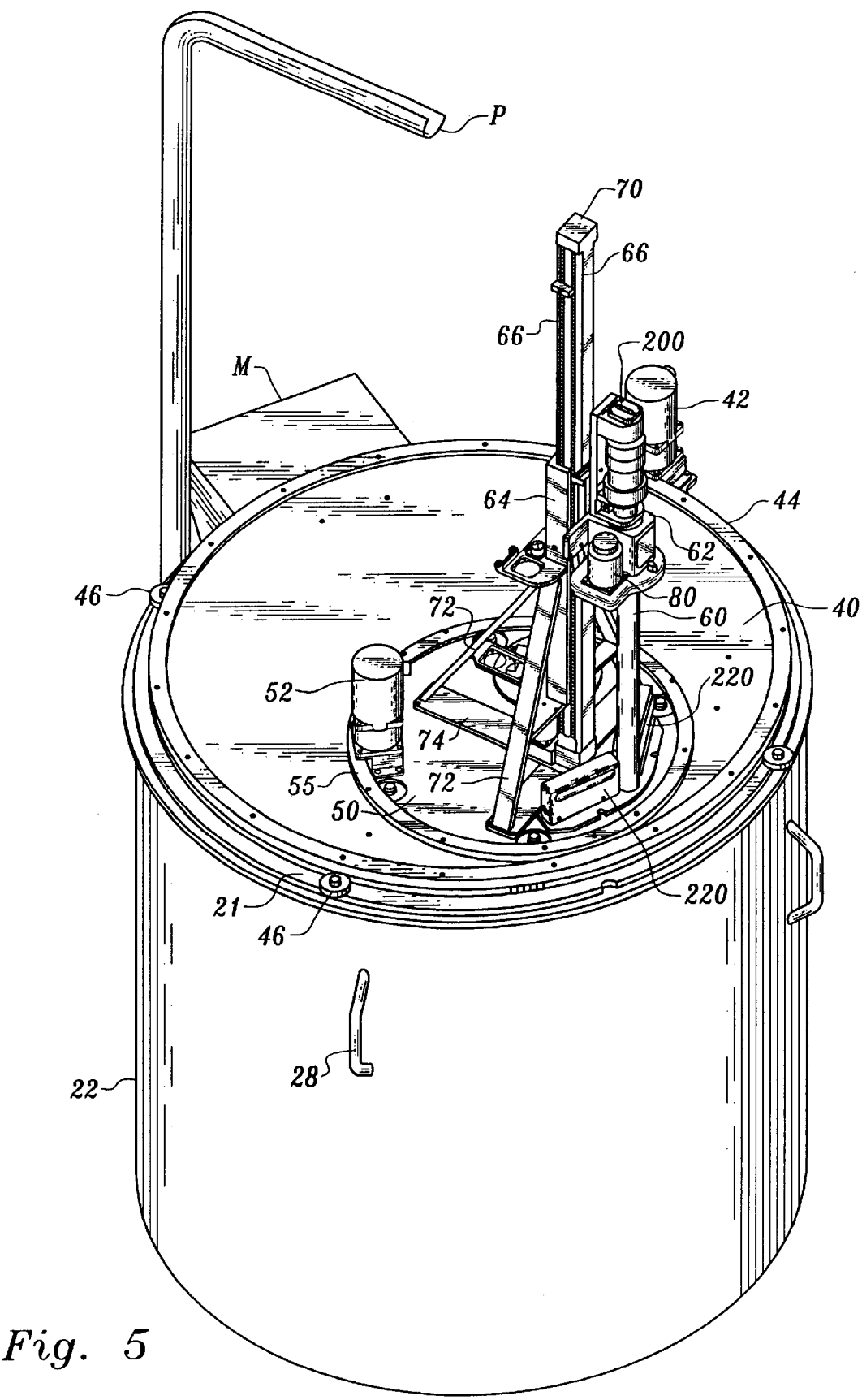
FIG. 5 is active view similar to FIG. 3 but from a different elevation.

FIGS. 3, 4, 5 and 6 reflect structure of a major lid 40 that occludes an open top of the dewar 22 and overlies rack lip 25. As shown in FIG. 3, the major lid 40 moves about the double-ended arrow "A". This is accomplished by a drive motor and gear head assembly 42 shown in FIGS. 4, 5 and 6. In essence, the motor 42 has a gear 43 on an output shaft which meshes with corresponding teeth 44 on a periphery of the major lid 40. The motor 42 is preferably mounted on rack lip 25 or could mount to dewar edge 21 or on a support flange. A series of pressure rollers 46 engage the periphery of the lid 40 to discourage wandering and excessive play by the lid. Alternatively, the drive motor and gear head assembly 42 can also use a roller in lieu of the gear arrangement if desired to drive the lid 40. As shown in FIGS. 4 and 5, the pressure rollers 46 are mounted on a top lip 25 of the rack 90 but could also mount on dewar top edge 21 or on a support flange. An overlying gantry post P (FIG. 5) supports cable for the freezer unit.

Figure 6:
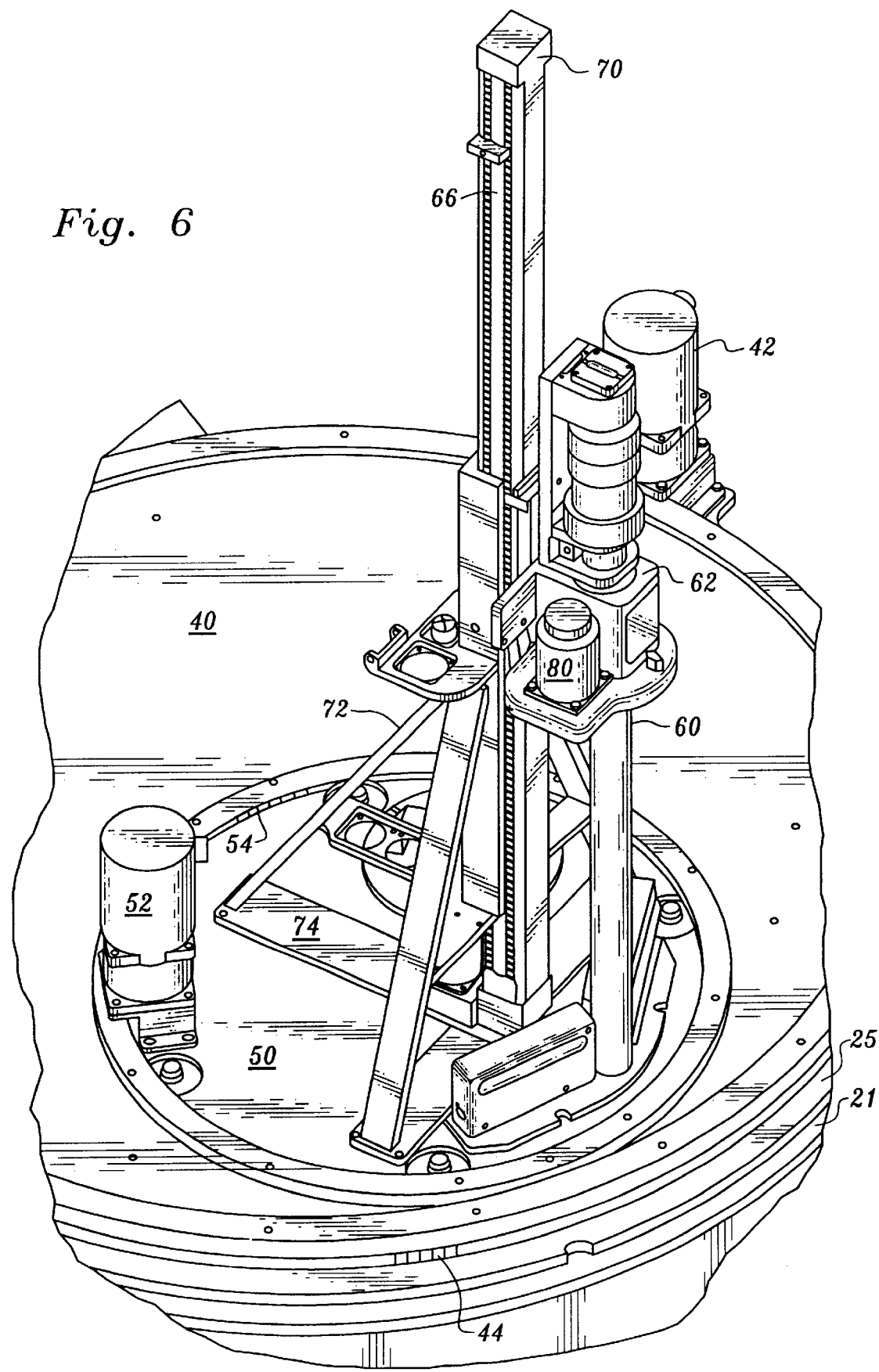
FIG. 6 is a view similar to FIG. 5, showing greater detail.

FIGS. 3, 5 and 6 also illustrate a minor lid 50 supported by a ring 55 on the major lid 40, but offset from a geometric center of the major lid 40. The lid 50 moves about the direction of the double-ended arrow "B". The minor lid 50 includes a minor lid motor 52 disposed on the minor lid 50 and having a gear output that drives teeth 54 carried on the ring 55 of the major lid 40.

The minor lid 50 supports the robotic arm and periscope 60. A free end 61 of the periscope 60 extends within the interior of the dewar 22 defining a robotic arm. The periscope 60 is supported on the minor lid 50 by means of a mast 70. The mast 70 includes triangulating braces 72 emanating from brace 64 for stability. The triangulating braces 72 terminate on a top surface of the minor lid 50 which includes horizontal braces 74 fixed on the minor lid 50. The periscope 60 is carried on the mast 70 via an elevator cage 62 which allows the periscope 60 to travel vertically along the double-ended arrows "C" of FIG. 3. The elevator cage 62 is enabled by a linear actuator 66 to allow the vertical travel along the direction of the double-ended arrow "C". Preferably the linear actuator is a threaded rod 66 passing through a complementally threaded bore of the elevator cage 62. Rotation of the threaded rod 66 causes the cage 62 to travel up or down.

In addition to pure vertical travel along the direction of the arrow "C", the periscope 60 is also capable of rotation about the double-ended arrow "D" shown in FIG. 3. More specifically, a periscope motor 80 is mounted on the elevator cage 62 which moves with the periscope 60 up and down as just described. In addition, the periscope motor 80 includes a gear drive that coacts with a peripheral gear on the periscope 60 to effect the rotation along the double-ended arrow "D".

The periscope 60, by virtue of its connection to the periscope motor 80 via its gear drive, the linear actuator 66 and rotation of both the minor lid 50 and major lid 40 accesses the interior of the dewar 22 with a great degree of precision. These different degrees of freedom for the periscope allow it to access all locations in the storage racks contained within the dewar.

Figure 7:
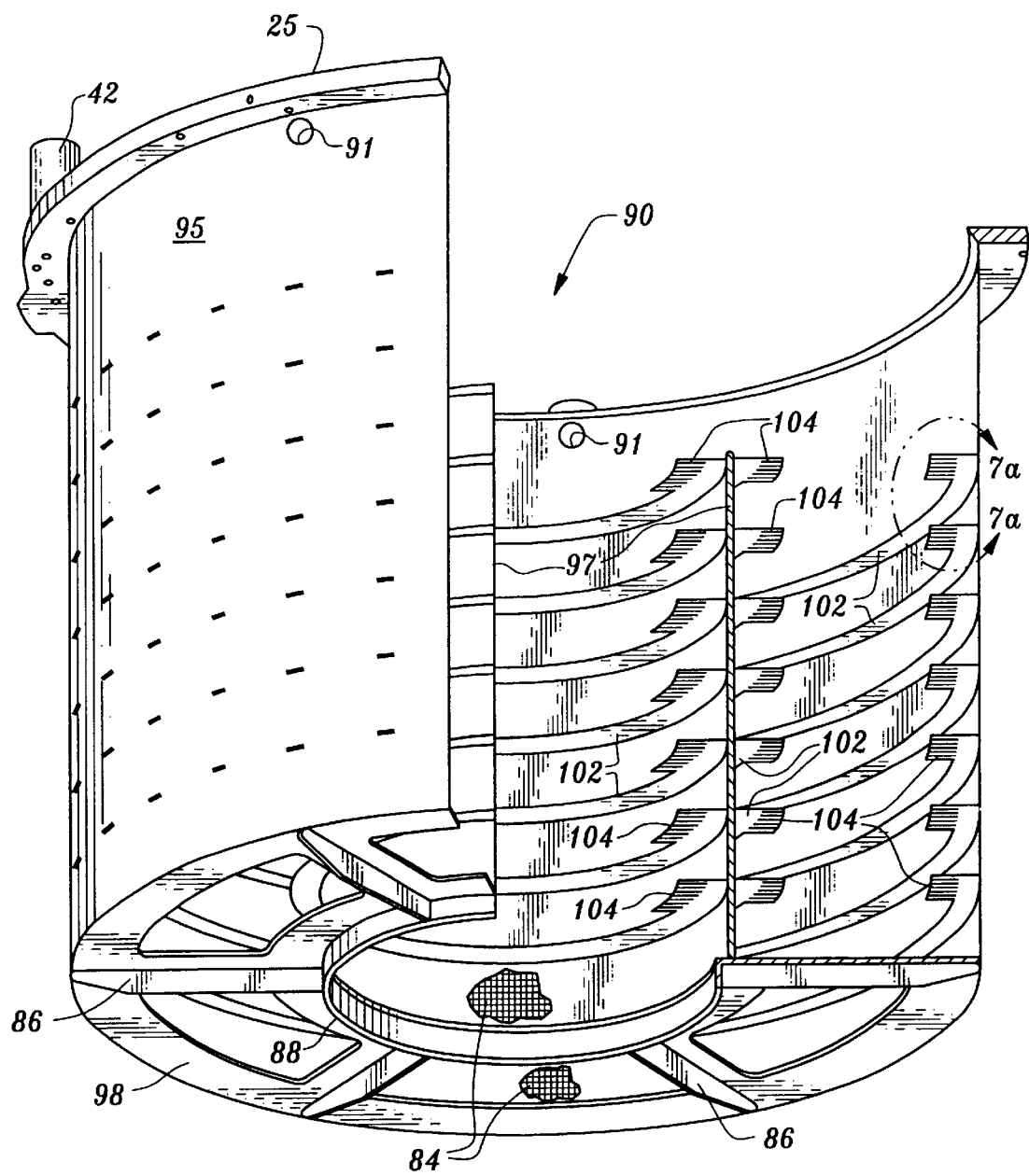
FIG. 7 is a partially fragmented perspective view of a storage rack removed from the dewar.
Figure 7A:
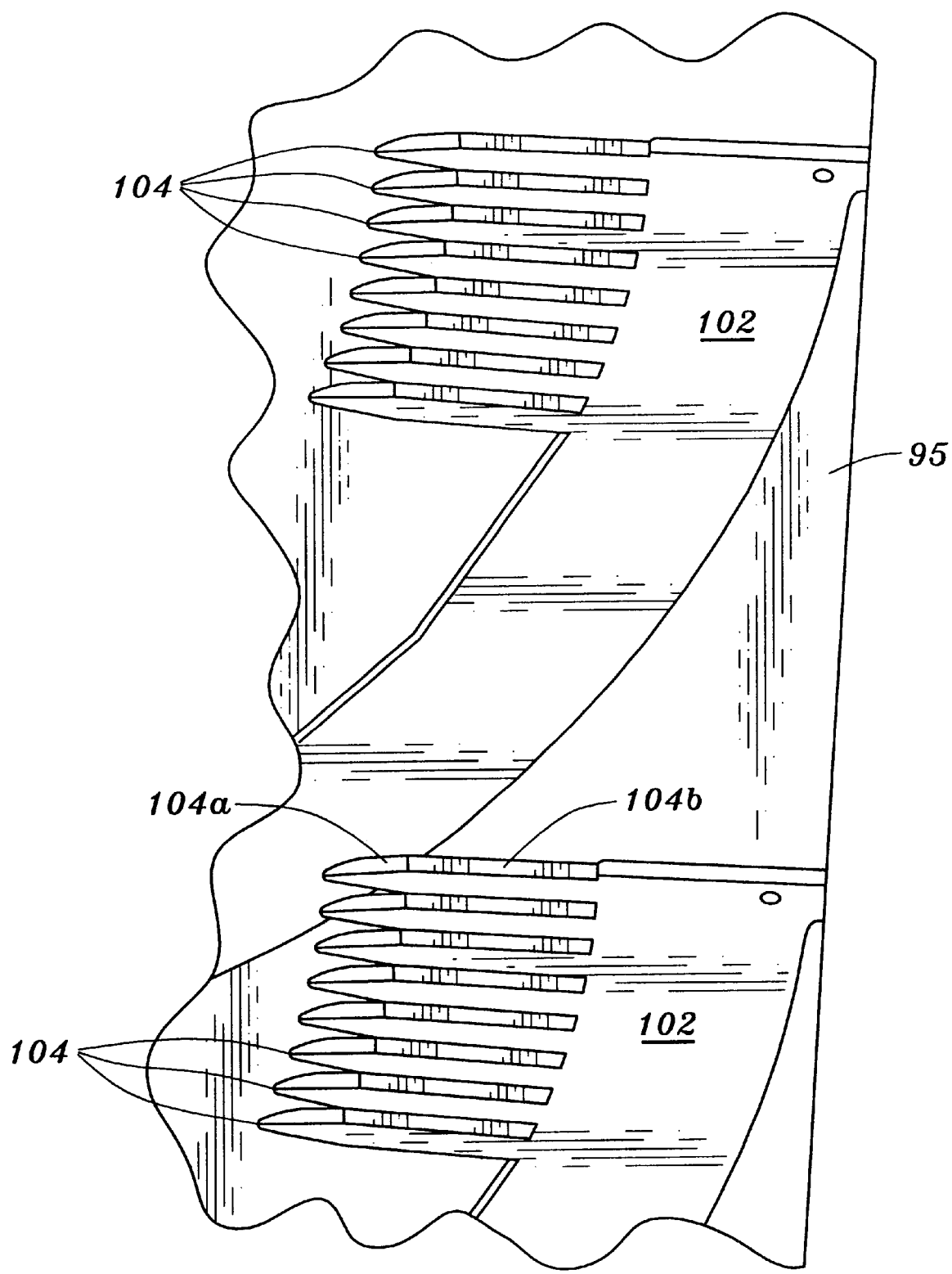
FIG. 7A details a fragment of FIG. 7 showing vertical tiers of a canister holding projections.

As shown in FIGS. 7, 7A, 8 and 9, the storage racks 92, 94, 96 are unitary 90 and can be removed and placed within the dewar 22 as a unit 90 as discussed with regard to the hook 93 and recesses 91 of FIG. 4. The storage rack 90 comprises a series of annular, cylindrical towers oriented in concentric relationship. More specifically, as shown in FIG. 7, an outermost annular tower 92 receives therewithin an inner cylindrical tower 94 that has, in abutting registry, a core annular tower 96 (FIG. 8) disposed therewithin. Core tower 96 circumscribes a central cylindrical void 103 to allow the robotic arm/periscope 60 access thereat, as does annular void 105 expose towers 92 and 94 to arm 60. The rack 90 is formed with an outer skin 95 that supports the lip 25 at its topmost extremity. Skin 95 is cylindrical. Peripheral bands 102 are fixed to the skin and project inwardly. Bands 102 support projections 104. Collectively the skin 95, band 102 and projections 104 define outermost annular tower 92.

FIG. 7 shows that on a bottom portion of the rack 90 a peripheral frame 98 communicates with a central core frame 88 by radiating ribs 86. A center area 103 of the core remains hollow. Mesh 84 is placed at the bottom wall of the rack 90 between the ribs 86 that extend between the central core 88 and the peripheral frame 98. Mesh 84 also spans the inner periphery of core frame 88. The purpose of the mesh (or perforations) is to decrease the rate at which the liquid nitrogen drains from the rack 90 should it be necessary to move the rack to another dewar. In such an event, hooks 93 are used to lift rack 90. A thermal blanket can drape the rack 90 in such an event to retain cold.

Ribs 86 and core 88 support towers 94 and 96. A common skin 97 extends between towers 94 and 96. Both the inner and outer surfaces of common skin 97 support their peripheral bands 102 which in turn supports projection 104. Please see FIGS. 7, 7A, 8 and 9.

In essence, and as shown in FIGS. 4, 7, 7A, 8 and 9 all towers are integrally formed with a plurality of projections 104 extending throughout each tower to allow the slideable insertion thereof of the product, especially when the product is encapsulated by a canister 110 to be described. The projections 104 are densely spaced next to each other with sufficient clearance therebetween to accommodate the canister 110. Please see FIG. 7A.

As shown in FIG. 8, product and the canister 110 are loaded along the direction of the several arrows "E". FIG. 8 also shows the periscope/robotic arm 60 at its free end 61, located within the dewar 22 supporting a canister 110 and addressing the storage racks 90. FIG. 9 reflects details of plural projections 104 one of which is to receive one canister 110 per projection as will be described. The projections 104 are located all along the height and periphery 102 of each tower to receive product as suggested by arrow "E". Clearances 103 and 105 for the robotic arm/periscope 60 allows the canisters to be received on the projections 104. The projections have a tapered leading end 104a that leads to a rectangular section 104b for reliable attachment to the canister 110.

Referring to FIGS. 10A through 10D the canister 110 is shown. The canister 110 is formed from two halves which are hinged together, one half is shown in FIG. 10C and another half in FIG. 10D. The half 112 shown in FIG. 10C includes a first planar wall 114 with a peripheral bottom wall 116, a side wall 118 and at top wall 120 forming a tray like structure having one side wall deleted. A corner 157 between bottom wall 116 and side wall 118 has been truncated. The edge 122 remote from side wall 118 has a slight curve leading towards both the top and bottom walls 120, 116. Both the top wall 120 and the bottom wall 116 (adjacent the "rolled" edge 122) include first and second holes 124 to receive a hinge 127 shown in FIGS. 10A and 10B. These holes 124 coact with holes 144 on the canister half 142 shown in FIG. 10D.

The planar wall 114 includes three upwardly extending raised portions 126 to precisely locate the product (described later) in a fixed position within the canister 110. The bottom wall 116 and top wall 120 each include pips 128 which project towards the planar wall 114 to frictionally engage complementarily formed recesses 148 on the other half 142. The side wall 118 includes a recess 130 to serve as a purchase area so that one can project one's finger therein to open the canister 110. The top wall 120 includes a central interruption where the wall 114 extends upwardly beyond the top wall 120, the wall extension 132 communicating with a raised wall 134 parallel to the top wall 120, but extending upwardly by a gap defined by the dimension of the wall extension 132. A rolled edge 136 projects downwardly towards the top wall 120 and parallel to the wall extension. Raised wall 134 includes a downwardly distressed portion 138 formed from resilient spring like material that serves as a friction catch 138 allowing secure retention on the projection 104 (FIG. 9) of the storage rack 90 just described. Rolled edge 136 assures that the projection 104 securely retains the canister 110 thereon and that the canister 110 will not shift laterally. When inserting the canister 110 on to a projection 104, the spring tension of the downwardly distressed portion 138 frictionally captures the projection 104 positively until the canister 110 is subsequently removed.

The other half 142 of the canister 110, shown in FIG. 10D, includes a second planar wall 154, a top wall 150 and a bottom wall 146. As mentioned, these top and bottom walls 146 and 150 include the holes 144 for the hinge 127 and also the holes 148 to receive the pips 128. In addition, an edge 152 adjacent the hinge (corresponding to edge 122) has a rolled contour facing up towards the top and bottom walls 150, 146. The edge opposite edge 152 includes an extension 156 running only a short distance down planar wall 154 from wall 150. Extension 156 raises a side wall 158 away from its counterpart 118 of FIG. 10C. A return 160 depends back towards its counterpart 118 and, as shown in FIG. 10A, has a length sufficient to frictionally contact the side wall 118 to provide a positive closure when the canister 110 is in the FIG. 10A closed position. Similar to FIG. 10C, FIG. 10D includes oval raised portions 126 projecting up from planar wall 154 to precisely locate the product in the canister 110. In addition, wall 154 includes a hole 162 allowing a temperature sensor (to be described) to project into the canister to monitor the temperature of the product as the temperature descends during controlled rate freezing. The return 160 in conjunction with the wall 158 and the wall 118 also serves as a passageway 170 (FIG. 10A) for the assembled canister 110 to allow a canister hook 172, FIG. 11 (located on the free end 61 of robotic arm/periscope 60), to pass therein in order to transport the canister 110 within the dewar 22 as will be described.

Referring to FIG. 12, the product bag 180 is shown. The product bag includes a main compartment 182 and a minor compartment 184. Typically, eighty percent of the volume is contained in the main compartment 182 with the remaining twenty percent in the minor compartment. The product bag 180 is of substantially rectangular shape and an area of demarcation 186 defined as a recess provides the division between the major compartment and the minor compartment. This recess 186 is dimensioned to straddle the canister raised portion 126a which is perpendicular to the other two. This will precisely locate the major compartment over the hole 162 so that a temperature probe can access the temperature of the product within the bag 180 and therefore monitor its decrease in temperature in a manner to be described. Bag 180 also includes two ports 188 separated from each other by a void 190. This void is also straddled by a raised portion 126b that is closest raised portion 126a. The remaining raised portion 126c locates the bag 180 precisely by its juxtaposition to a recess 192 which spans between one inboard port 188a and fluidic column 194 which projects out of the bag. Column 194 includes an elbow 196 leading at a right angle to a linear section 198 that overlies inboard port 188a. In other words, it is preferred that the bag 180 only be inserted into the canister 110 in one orientation so that the hole 162 in the canister 110 can address only the main compartment 182. This increases the precision in following a cooling regimen because the temperature probe is monitoring the largest volume in the bag 180 at its centerpoint.

Referring to FIGS. 11 and 13, the periscope and robotic arm 60 includes an elongate cylindrical column preferably hollow and filled either with a gas such as nitrogen or drawn with a vacuum to promote optical clarity and minimize condensation or other opacity. At topmost portion of the periscope includes a lens and a bar code reader 200 which receives information with respect to a bar code label 202 located on the canister 110 overlying an outer surface of wall 158. The free end 61 of the periscope 60 includes an optical portal 204 located preferably near a canister hook 172 of FIG. 11. It is preferred that a source of light 207, preferably an LED or perhaps a laser be adjacent the portal 204. Thus, the bar code label 202, being located on the canister receiver 170, will address the light 207 and portal 204 after the canister hook 172 of the free end 61 lodges in the receiver 170. Note that a face of the hook 172 which faces the portal 204 has its own distinctive bar code 202a. When the canister hook 172 has nested within the receiver 170 on the canister 110, the portal 204 and light 207 will no longer address the bar code 202a of the hook, but instead will scan a bar code label 202 as shown in FIG. 13 and transmit the information up the periscope tube 60 and to the lens and bar code reader 200. This feature provides positive feedback that the canister 110 is properly secured on the hook 172. Thus, light 201 from LED 207 passes through a portal 204 reflects on bar code 202 (or 202a) and is then diverted via a mirror 206 at a bottom portion of the free end 61 of the periscope 60, to then reflect back light 201 (modified by the bar code identity) to the lens and reader assembly 200.

Figure 14:
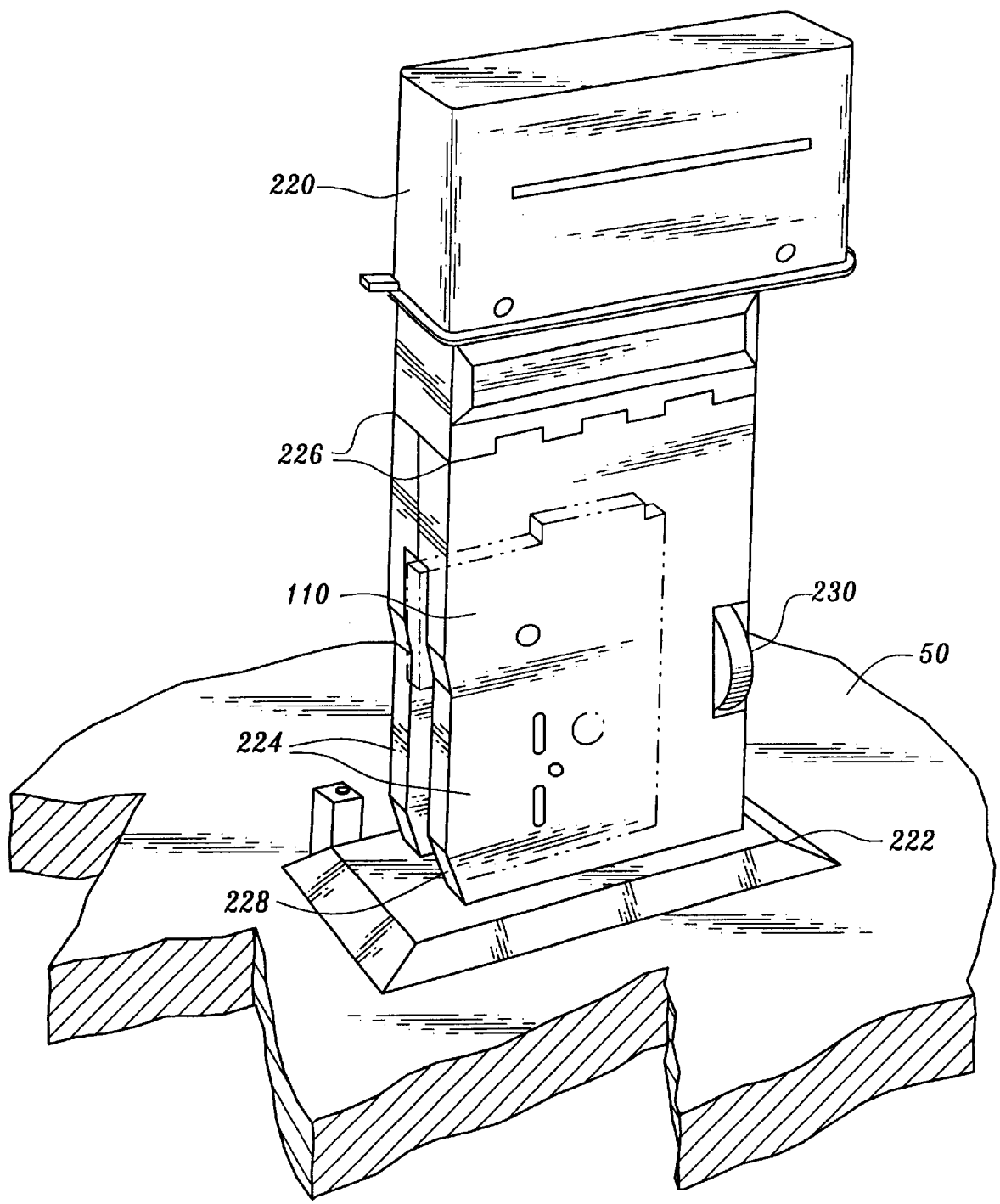
FIG. 14 is a perspective view of the freezer module and its orientation adjacent a minor lid the system in order to deploy a canister into the dewar.
Figure 15:
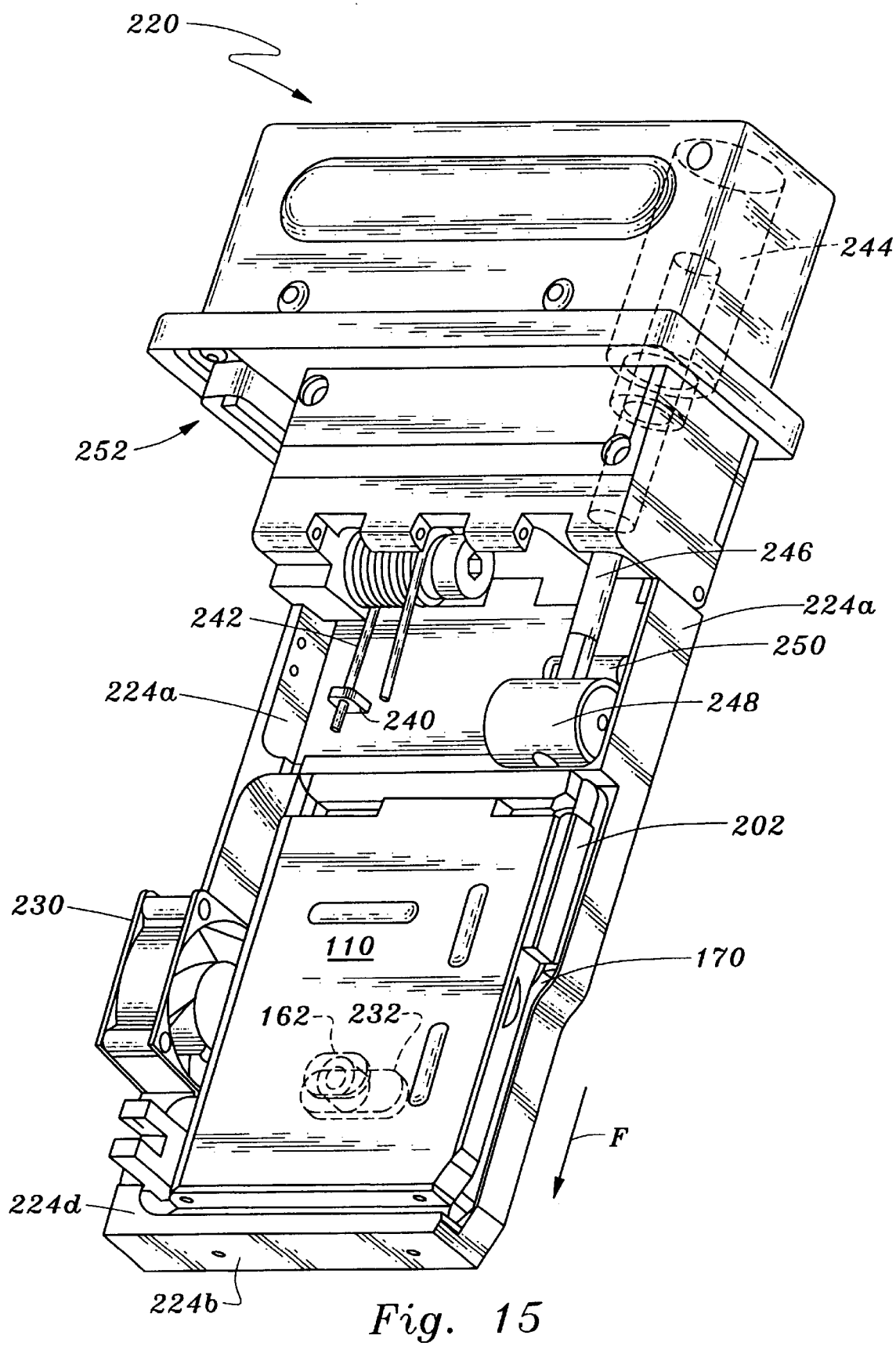
FIG. 15 is a perspective view of the freezer module of FIG. 14, with one door removed to expose interior detail.
Figure 16:
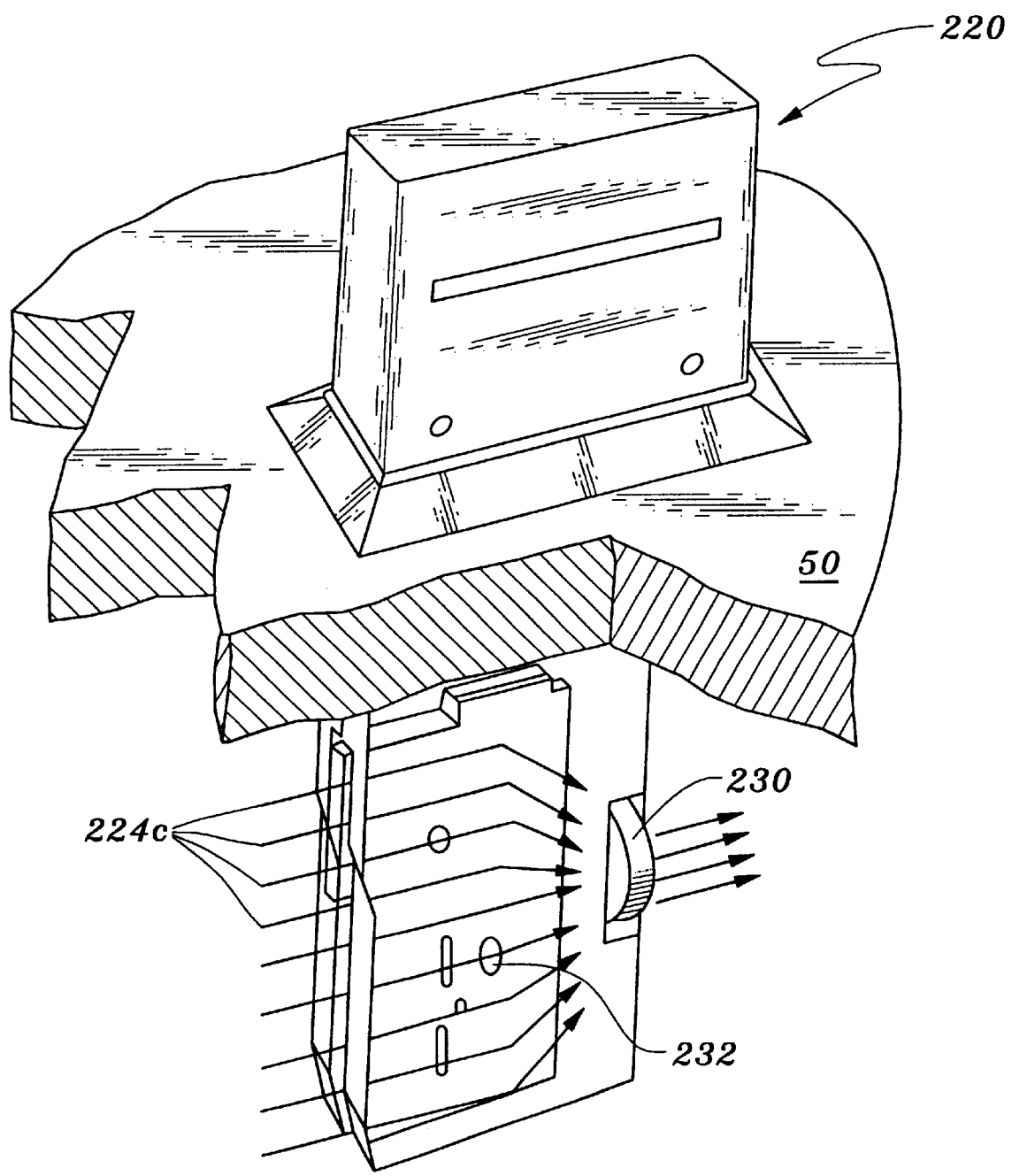
FIG. 16 is a perspective view of the freezer control module deployed in the dewar allowing controlled rate freezing.

FIGS. 14 through 16 depict a manner in which the canister and its product are inserted into the dewar through the freezer module 220. As shown in FIG. 14, a port 222 passes through the minor lid 50. When the freezer module 220 is not deployed there, an insulative plug is placed in its stead. The freezer module 220 includes a lower portion provided with retention plates 224 which open about hinges 226 on both sides thereof allowing access to the canister 110 contained therewithin. Notice how a mitered corner 228 corresponds to the truncated corner 157 of the canister 110. This is one way of assuring proper orientation of the canister 110 within the control module 220. FIG. 14 also depicts a fan 230. Details of the interior of the control module 220, under the retention plates 224, are explored in FIG. 15. Each of the retention plates hold the canister 110, act as doors 224 and include side walls 224a and a bottom wall 224b. Two side walls 224a are shown on opposite sides of one door 224 in FIG. 15. Clearance is provided in one side wall 224a for a fan 230 that draws cold nitrogen gas through flow channels (224c of FIG. 16) to pass over the canister 110. A temperature measuring device 232 mounted on one or both of the doors 224 passes its probe into the canister 110 through the hole 162 provided on the canister 110 and discussed hereinabove for monitoring the temperature profile of the main compartment 182 of the bag 180. The probes of the temperature measuring device 232 monitors the temperature excursion of the product within the bag 180 until the product has conformed to an illustrative curve in FIG. 17 which corresponds to a preferred freeze profile illustrative of a preferred model for white stem cells. The probe also partially supports the canister 110 in conjunction with bottom walls 224b. Only after the periscope hook 172 supports the canister 110 by its receiver 170, as signaled by the change in the bar code (from 202a to 202) will the doors will surrender the canister 110 to the periscope 60.

Figure 17:
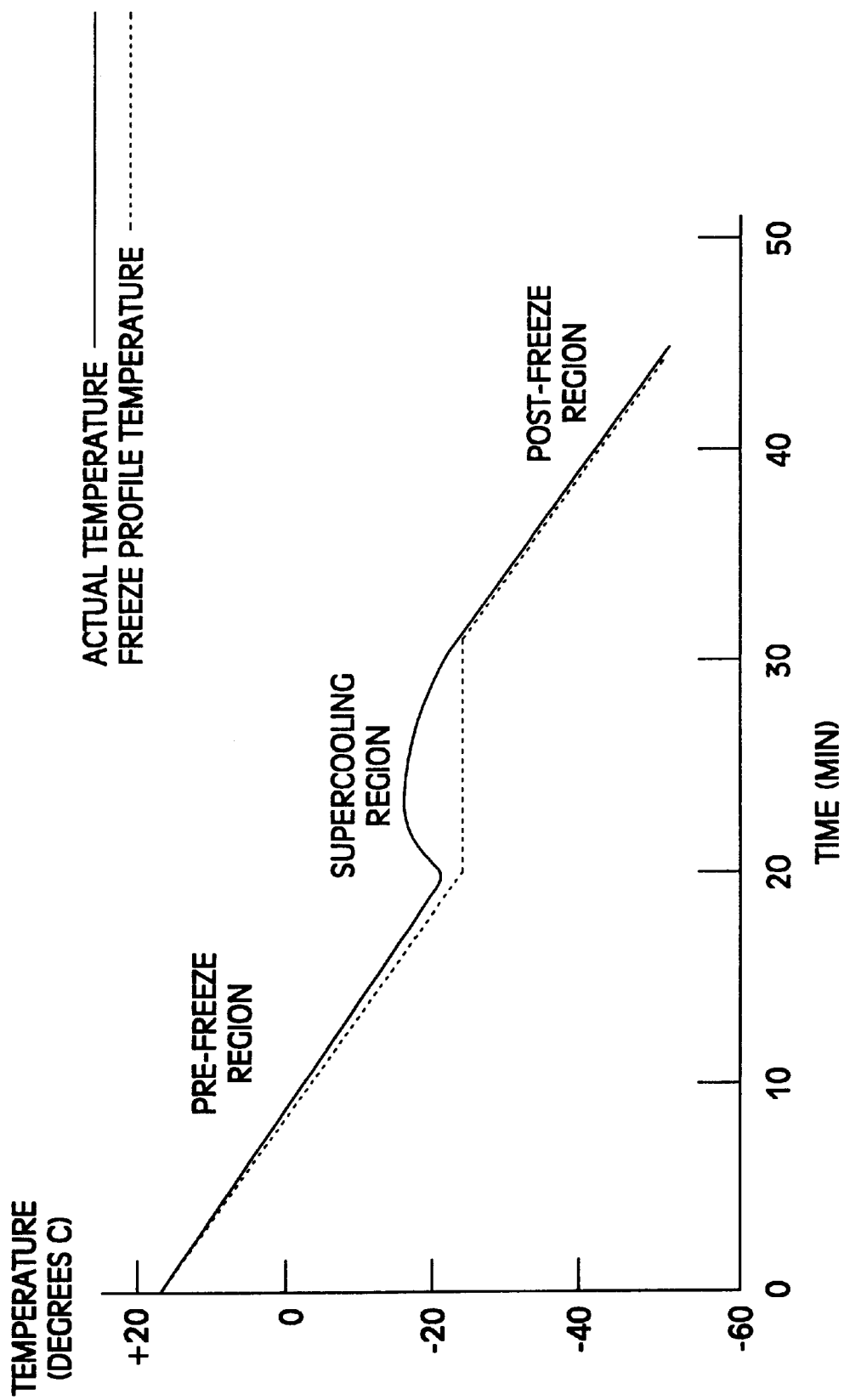
FIG. 17 is a graph exemplifying one freezing profile according to the present invention.

As shown in FIG. 17, because there is cryoprotectant mixed in with the white stem cells, the freezing temperature is about −20° C. (the super cooling region). This is an area where greater time should be allowed for the phase change of the product since gentle cooling at that time is most beneficial to prevent the formation of ice crystals which can injure the contents within the bag 180. During the cooling process, the fan's speed operates at a rate which can be varied in order to have the time profile of FIG. 17 become optimized. The cold nitrogen vapor 224c depicted flowing in FIG. 16 finally lowers the temperature of the product in the bag 180 to approximately −50° C. at which point the fan 230 stops, hook 172 supports canister 110 and the doors 224 open.

Referring again to FIG. 15, each door 224 includes an apertured post 240 on an inner surface which receives a leg of a coil spring 242 passing through the aperture. The spring 242 is biased such that the doors want to stay in the closed position. Once the freezer module 220 has determined, via the temperature measuring device 232, that the appropriate temperature has been reached, a command is sent to a solenoid 244 located in freezer module 220 which in turn activates a plunger 246 that causes a bearing 248 located at an extremity of the plunger 246 remote from the solenoid 244 to operate against a bearing surface 250 to force the doors 224 open against the pressure of the spring 242. Because the canister 110 is now retained by the projection hook 172 on the periscope 60, it removes the canister by motion in the direction of the arrow "F" away from the controlled rate freezer module 220 and seeks a location in the storage racks 90 as set forth hereinabove.

In use and operation, a bag 180 of the product is delivered to the system 10 of FIG. 1. The bag 180 (FIG. 12) is provided with a bar code label 202. A bar code scanner 300 reads the label 202. The bar code label printer 310 prints a corresponding label for the canister 110. The operator verifies the correspondence between the printed label of both the canister 110 and the bag 180. The computer 320 (after an approved operator has logged on and provided an access password) notes the desire to place a bag 180 now contained within the canister 110 into the system 10. A controlled rate freezer module 220 accepts the canister 110 with the product and bag 180 loaded and ready to go. Once the freezer module 220 is inserted through the minor lid 50 of the dewar 22, a temperature profile specific to the product being frozen is selected by the operator and downloaded from the computer to the controlled rate freezer module 220. Note the electrical connection 252 (FIG. 15) which allows the freezer module 220 to communicate to the computer 320. Next, the cooling process begins until complete. Next, the periscope 60 addresses the canister 110 within the freezer module 220, access having been gained before the freezer module doors 224 are opened. The hook 172 on the periscope 60 engages the canister 110. The reading head 204 of the periscope 60 corresponds the bar code back 202 to the computer 320. So long as the periscope is reading the correct bar code 202 (and not its own code 202a) the doors 224 open. The computer then directs the periscope to a location within the dewar 22 and records a specific address for that canister within the storage rack 90. The periscope 60 deploys the canister 110 on a projection 104 of the storage rack 90. The canister 110 and product within the bag 180 hereby safely maintained.

A control module 360 (FIG. 2) located on the dewar 22 monitors the temperature within the dewar 22, perhaps the vacuum between the spaced walls 22a, 22b and the liquid level of the nitrogen. The control module 360 includes a standby power source P should there be a power interruption. The control module 360 includes an alarm L if there is an undesirable temperature excursion, a loss of liquid nitrogen or a problem with the vacuum between the walls of the dewar. The control module 360 can replenish the liquid nitrogen via a valve V in fluid communication with a source of nitrogen (not shown) if needed.

Moreover, having thus described the invention, it should be apparent that numerous structural modifications and adaptations may be resorted to without departing from the scope and fair meaning of the instant invention as set forth hereinabove and as described hereinbelow by the claims.

What is claimed is:

1. A canister for a thermolabile product which allows the thermolabile product to be contacted by a robotic arm, comprising, in combination:
   means for attaching said canister to said thermolabile product, and means for attaching said thermolabile product to said robotic arm through said canister.

2. The canister of claim 1 including a surface upon which indicia is disposed thereon, said surface having a longitudinal edge and a latitudinal edge,
   a downwardly depending side wall from one said longitudinal edge and a hairpin turn at a terminal portion of said side wall extending upwardly to a free end, adjacent another longitudinal edge, said canister formed from resilient material to frictionally grasp the thermolabile product.

3. The canister of claim 1 including:
   a receiver to accept the thermolabile product,
   a door on said receiver to occlude and protect the thermolabile product when said door is closed,
   indicia on said canister readable by means on said robotic arm to correlate with the product.

4. The canister of claim 1 including a retention means on said canister for fixed attachment in a storage site.

5. The canister of claim 1 including:
   said canister having indicia associated therewith correlative of indicia on said thermolabile product and means on said robotic arm for reading said indicia.

6. The canister of claim 1 including:
   two halves which are hinged together, one half includes a first planar wall with a peripheral bottom wall, a side wall and a top wall forming a tray like structure, said top wall and said bottom wall include first and second holes to receive a hinge;
   an other half of said canister includes a planar wall, a top wall and a bottom wall, said other half top and bottom walls include holes for said hinge.

7. The canister of claim 6 further including frictional engagement means between said halves to secure said canister in closed relationship.

8. The canister of claim 6 including projection receiving means defining a wall extension emanating from said half planar wall, a raised wall parallel to said top wall and emanating from said wall extension, a rolled edge depending from said raised wall projecting towards said canister, and a resilient spring catch depending from said raised wall to provide spring pressure on the projection.

9. The canister of claim 6 wherein said robotic arm attaching means includes an extension emanating from said planar wall of said other half, a raised side wall supported by said extension and a return supported by said side wall to form an open ended channel to receive said robotic arm.

10. The canister of claim 6 including pips located on walls of one said half oriented in registry with corresponding recesses on said other half for holding said canister closed.

11. The canister of claim 6 including a finger purchase recess located on said side wall of said one half.

12. The canister of claim 1 further comprising:
    projection receiving means to allow a projection to retain said canister.

13. The canister of claim 12 wherein said projection receiving means includes a resilient spring catch to frictionally bear against the projection.

14. The canister of claim 1 further including temperature probe receiving means passing through said canister.

15. A canister, comprising, in combination:
    two halves which are hinged together, one half includes a first planar wall with a peripheral bottom wall, a side wall and a top wall forming a tray like structure, said top wall and said bottom wall include first and second holes to receive a hinge;
    an other half of said canister includes a planar wall, a top wall and a bottom wall, said other half top and bottom walls include holes for said hinge;
    projection receiving means to allow a projection to retain said canister;
    robotic arm receiving means to allow a robotic arm to transfer said canister;
    frictional engagement means between said halves to secure said canister in closed relationship; and
    temperature probe receiving means passing through said canister.

16. The canister of claim 15 further including means for precisely orienting a product bag within said canister.

17. The canister of claim 16 wherein said precise orienting means includes raised oval portions in said planar walls, two oval portions axially aligned and one oval portion perpendicular to said two oval portions.

18. A canister, comprising, in combination:
    two halves which are hinged together, one half includes a first planar wall with a peripheral bottom wall, a side wall and a top wall forming a tray like structure, said top wall and said bottom wall include first and second holes to receive a hinge;
    an other half of said canister includes a planar wall, a top wall and a bottom wall, said other half top and bottom walls include holes for said hinge;
    projection receiving means to allow a projection to retain said canister;
    wherein said projection receiving means includes a resilient spring catch to frictionally bear against the projection;
    wherein said projection receiving means includes a wall extension emanating from said half planar wall, a raised wall parallel to said top wall and emanating from said wall extension, a rolled edge depending from said raised wall projecting towards said canister, and a resilient spring catch depending from said raised wall to provide spring pressure on the projection.

19. A canister, comprising, in combination:
    two halves which are hinged together, one half includes a first planar wall with a peripheral bottom wall, a side wall and a top wall forming a tray like structure, said top wall and said bottom wall include first and second holes to receive a hinge;
    an other half of said canister includes a planar wall, a top wall and a bottom wall, said other half top and bottom walls include holes for said hinge;
    projection receiving means to allow a projection to retain said canister;

robotic arm receiving means to allow a robotic arm to transfer said canister;

wherein said robotic arm receiving means includes an extension emanating from said planar wall of said other half, a raised side wall supported by said extension and a return supported by said side wall to form an open ended channel to receive the robotic arm.

20. A canister, comprising, in combination:

two halves which are hinged together, one half includes a first planar wall with a peripheral bottom wall, a side wall and a top wall forming a tray like structure, said top wall and said bottom wall include first and second holes to receive a hinge;

an other half of said canister includes a planar wall, a top wall and a bottom wall, said other half top and bottom walls include holes for said hinge;

projection receiving means to allow a projection to retain said canister;

frictional engagement means between said halves to secure said canister in closed relationship; and pips located on walls of one said half oriented in registry with corresponding recesses on another half for holding said canister closed.

21. A canister, comprising, in combination:

two halves which are hinged together, one half includes a first planar wall with a peripheral bottom wall, a side wall and a top wall forming a tray like structure, said top wall and said bottom wall include first and second holes to receive a hinge;

an other half of said canister includes a planar wall, a top wall and a bottom wall, said other half top and bottom walls include holes for said hinge;

including a finger purchase recess located on said side wall of said one half.

* * * * *